(12) United States Patent
Kandora

(10) Patent No.: US 7,103,932 B1
(45) Date of Patent: Sep. 12, 2006

(54) ECHOCARDIOGRAPHY TABLE SWING OUT PATIENT SUPPORT CUSHION

(75) Inventor: James M. Kandora, Port Jefferson Station, NY (US)

(73) Assignee: Biodex Medical Systems, Inc., Shirley, NY (US)

( * ) Notice: Subject to any disclaimer, the term of this patent is extended or adjusted under 35 U.S.C. 154(b) by 62 days.

(21) Appl. No.: 11/012,538

(22) Filed: Dec. 15, 2004

(51) Int. Cl.
A47B 16/00 (2006.01)

(52) U.S. Cl. .................... 5/613; 5/621; 5/623
(58) Field of Classification Search ............ 5/621–624, 5/613
See application file for complete search history.

(56) References Cited

U.S. PATENT DOCUMENTS

| 222,455 | A | | 12/1879 | Mendhanm |
|---|---|---|---|---|
| 395,001 | A | | 12/1888 | Russell |
| 1,040,795 | A | | 10/1912 | Skeffington |
| 1,274,851 | A | | 8/1918 | Byrd |
| 1,891,599 | A | | 12/1932 | Kushner |
| 2,103,693 | A | | 12/1937 | Pohl |
| 2,258,782 | A | * | 10/1941 | McKean ................. 5/623 |
| 2,897,029 | A | | 7/1959 | Maisel |
| 3,265,432 | A | | 8/1966 | Tabbert |
| 3,652,851 | A | | 3/1972 | Zaalberg |
| 3,795,018 | A | | 3/1974 | Broaded |
| 3,840,221 | A | | 10/1974 | Hogan |
| 3,973,126 | A | | 8/1976 | Redington et al. |
| 4,620,333 | A | | 11/1986 | Ritter |
| 4,973,034 | A | | 11/1990 | Michele |
| 5,133,097 | A | | 7/1992 | Pyles |
| 5,184,363 | A | | 2/1993 | Falbo, Sr. |
| 5,742,962 | A | | 4/1998 | Yoshino et al. |
| 6,195,820 | B1 | * | 3/2001 | Heimbrock et al. ........ 5/623 |
| 6,260,220 | B1 | | 7/2001 | Lamb et al. |
| 6,615,430 | B1 | | 9/2003 | Heimbrock |
| 2002/0056161 | A1 | | 5/2002 | Falbo, Sr. et al. |

* cited by examiner

Primary Examiner—Patricia Engle
Assistant Examiner—Fredrick Conley
(74) Attorney, Agent, or Firm—Gibbons, Del Deo, Dolan, Griffinger & Vecchione

(57) ABSTRACT

Echocardiography table with an access cushion hinged within an access recess and a patient support cushion that swings out about a pivot from a swung in position within a patient support recess and a swung out position clear of the patient support recess. Retainers such as locking elements keep the patient support cushion in either the swung in or swung out position, as applicable. The patient support recess may have opposite walls that diverge and complement the tapering sides of the patient support cushion. The access cushion may be hinged to either rotate upright or swing to a hanging position.

17 Claims, 6 Drawing Sheets

ECHOCARDIOGRAPHY TABLE SWING OUT
PATIENT SUPPORT CUSHION

BACKGROUND OF THE INVENTION

1. Field of the Invention

The present invention relates to an echocardiography table with movable cushions to allow a sonographer closer access to the patient and still provide comfort to the patient.

2. Description of Related Art

An echocardiography procedure is often performed on a special table with movable cushions to allow the sonographer closer access to the patient. During the procedure, the sonographer has to press a transducer firmly against the patient's chest and back in several positions to obtain an ultrasound image of the heart. The patient lies on his/her left side facing away from the sonographer.

Conventional tables have a movable cushion that rotates down or up to allow the sonographer closer access to the patient. These same tables have a second patient support cushion that is initially under the patient and then rotated down or pulled out in the area of the patient's chest to allow better access. As a result of rotating down or pulling out, an opening forms in the table. There are issues of patient comfort as the patient lies across this opening, because the patient has to hold his/her arms while hanging over the side of the cushion.

It is desired to provide a patient support table with a patient support cushion that swings between a swung in position within a recess and a swung out position clear of the recess. In the swung in position, it would be desirable for the patient support cushion to support the chest of the patient while the patient lies on his/her side. It would be desirable for the patient support cushion to support the patient's arms while the patient lies on his/her side.

BRIEF SUMMARY OF THE INVENTION

One aspect of the invention resides in a table having a recess and a patient support movable about a pivot between a swung in position within the recess and a swung out position substantially clear of the recess, the patient support being supported at the pivot at a support location spaced from the pivot when in the swung in position and at a further location spaced from the pivot when in the swung out position. The patient support may be locked in the swung in and swung out positions and unlocked under manual force. The table and patient support may be cushioned to stably support the weight of a patient lying across the table and the patient support when the patient support is locked in the swung in position. The patient support may stably support more weight than just the arm of the patient when locked in the swung out position.

BRIEF DESCRIPTION OF THE DRAWINGS

For a better understanding of the present invention, reference is made to the following description and accompanying drawings, while the scope of the invention is set forth in the appended claims.

DETAILED DESCRIPTION OF THE INVENTION

Figure 1:
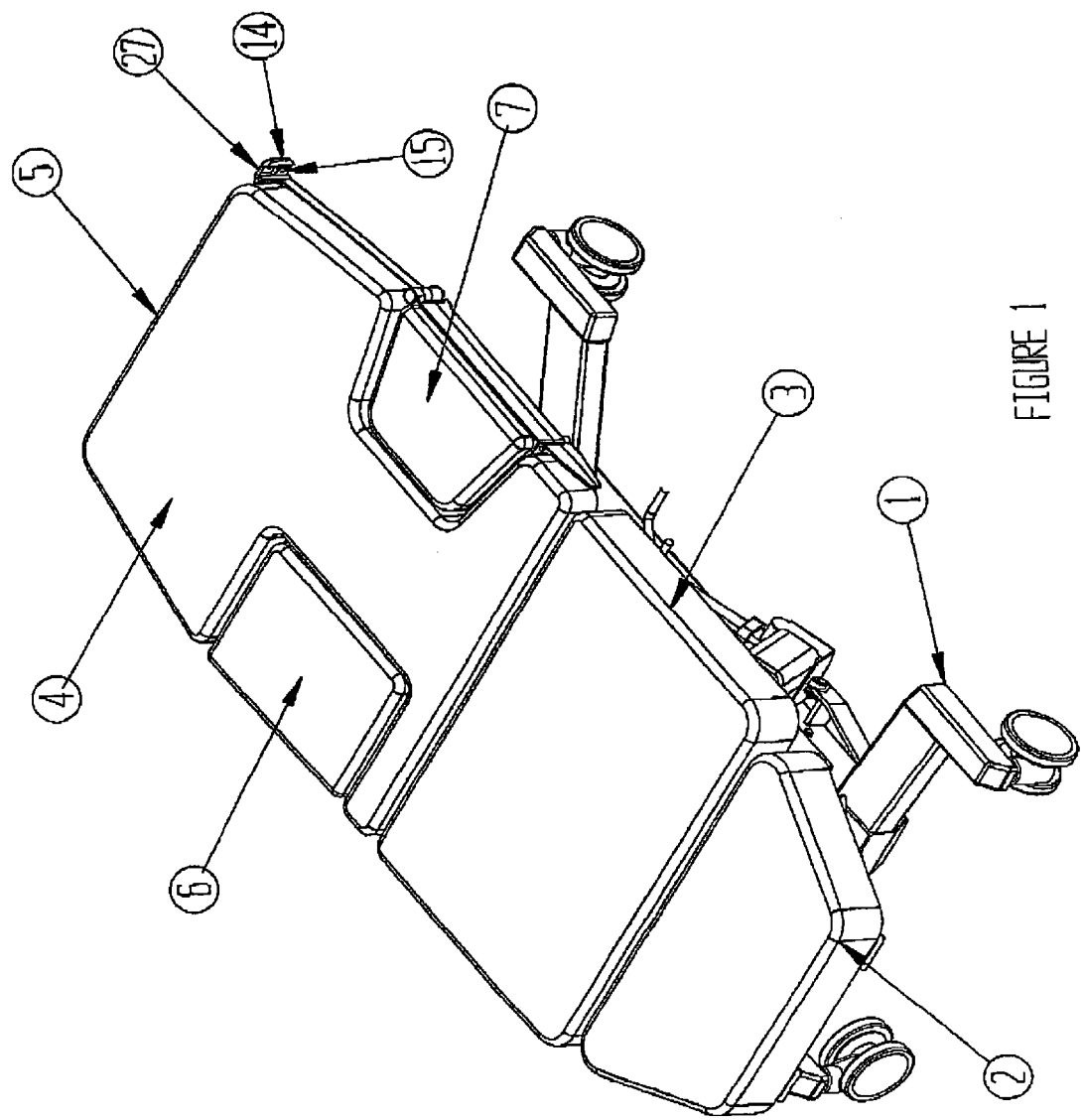
FIGS. 1–4 are top isometric views of the echocardiography table according to the invention showing the movable cushions in various positions.
Figure 2:
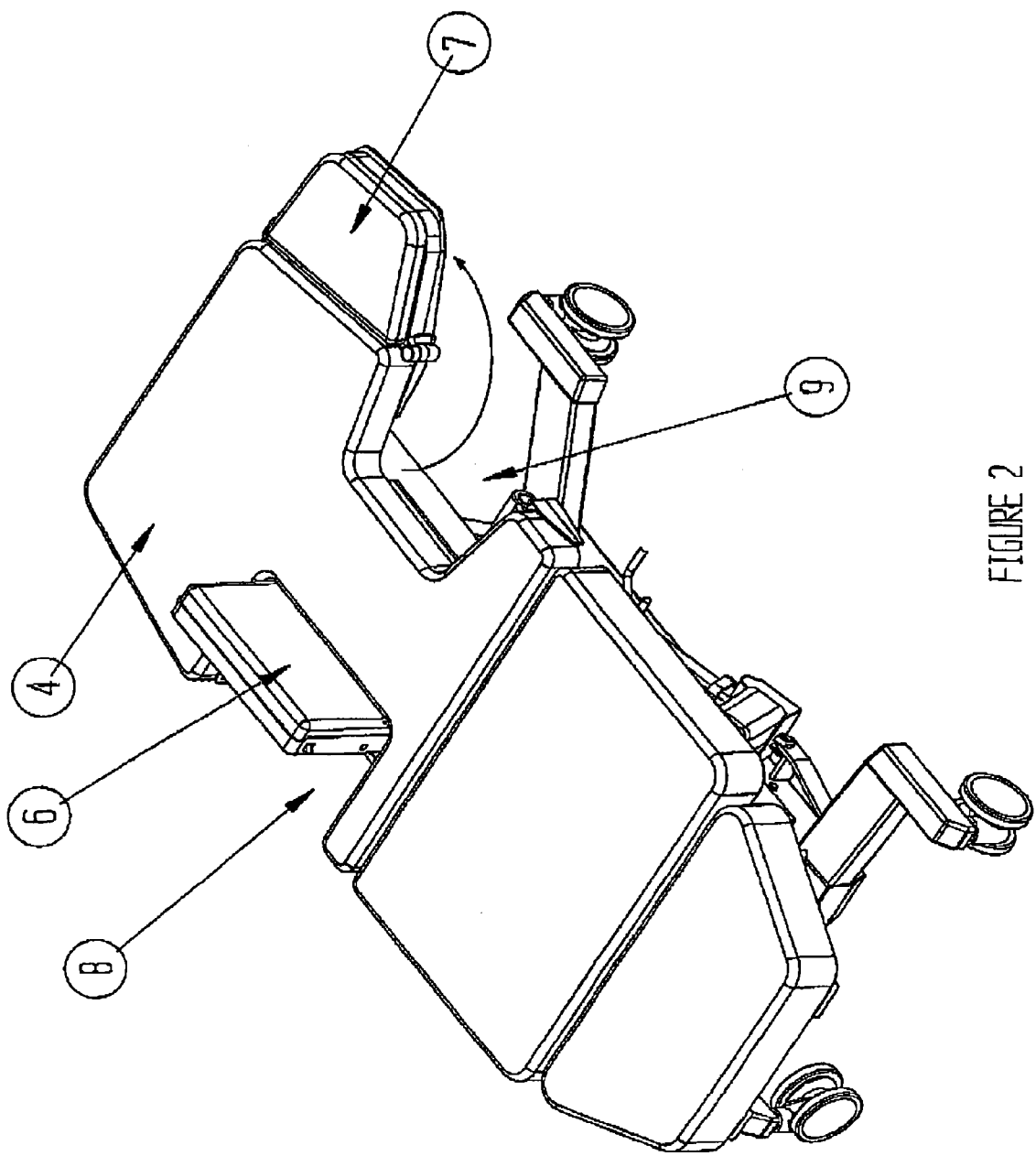

Turning to the drawings, FIGS. 1 and 2 show a table with a base frame 1 that supports an upper frame (not shown). The upper frame supports a foot cushion 2, a base cushion 3 and a fowler back assembly 4. The patient lies on their left side with their head toward the head end 5 of the fowler back assembly 4. The fowler back assembly has an access cushion 6 and a patient support cushion 7 rotatably attached to respective pivots. The access cushion 6 is shown within an access recess 8. The patient support cushion 7 is shown in a swung in position within a patient support recess 9, where it will support the patient's chest as the patient lies on his/her left side.

As shown in FIG. 2, the access cushion 6 is rotated upwards on the fowler back assembly 4 into an upright orientation and locked in place. In this position, the sonographer may enter the opening defined by the access recess 8 to lean and better reach around the patient. The patient may also lean his/her back against the access cushion 6 while lying on his/her left side.

Figure 4:
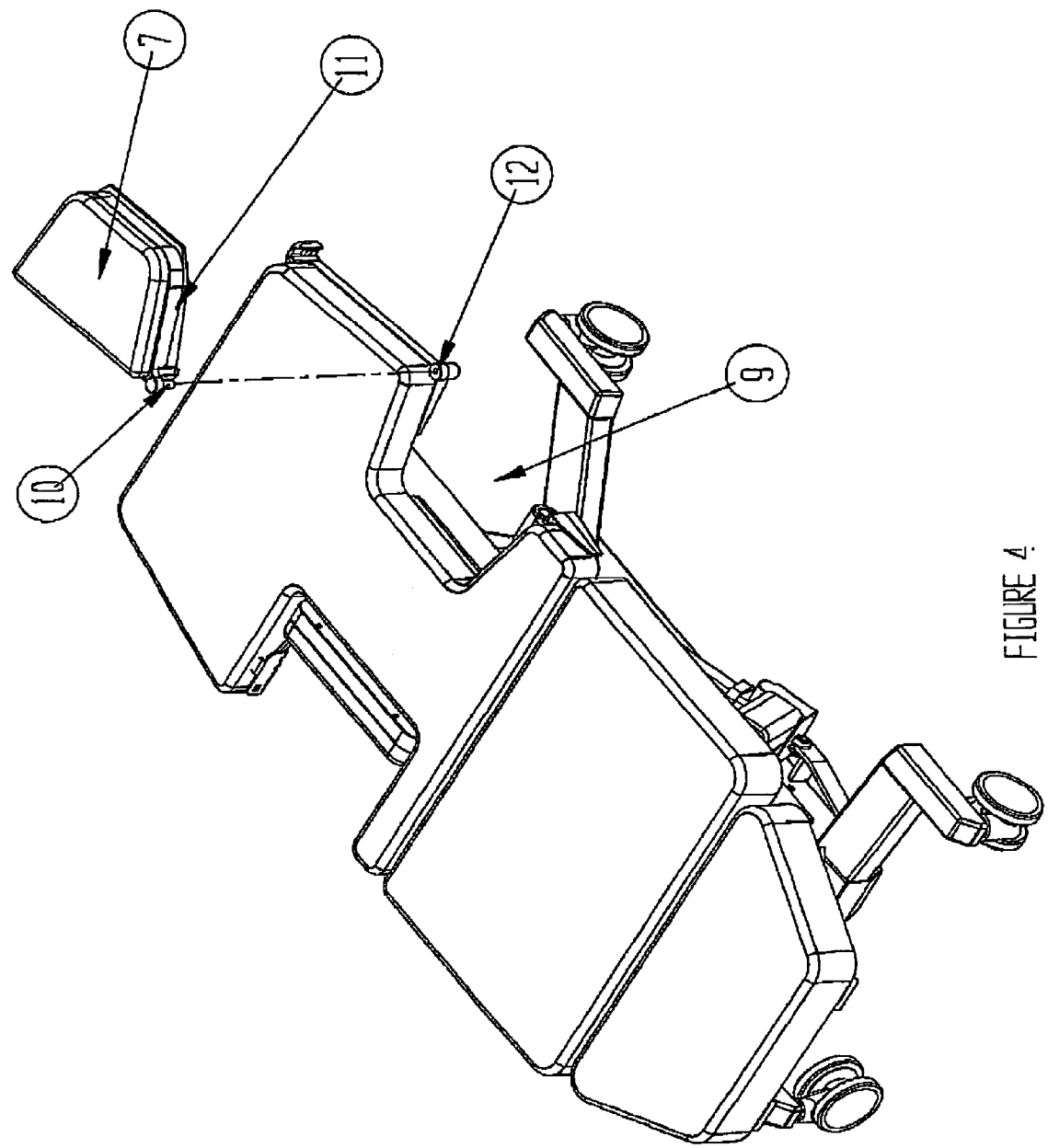

FIG. 2 also shows how the patient support cushion 7 swings out from the fowler back assembly 4 to form a table extension that the patient can rest their arms on. The patient support access or opening 9 that is created with the patient support cushion 7 in this position allows the sonographer to reach all the way around the patient's chest to position the ultra sound transducer. Turning to FIG. 4, a pivot for swinging of the patient support cushion 7 is formed by a hinge pin 10, which is part of the patient support base 11, and the hinge knuckle 12, which is an integral part of the hinge casting 13, which in turn is mechanically fastened to the fowler back assembly 4. The pivot is at a boundary between being within the recess and being without the recess.

The opening 9 is bounded by a border that may have opposite walls that diverge outwardly. The patient support cushion 7 may have opposite sides that taper inwardly (or diverge outwardly) and configured to complement the shape of the opposite walls of the border that taper inwardly (or diverge outwardlly). The patient support cushion 7 may have a trapezoidal shape in cross section with rounded corners as depicted in the figures. However, many other shapes are available to be used instead as long as the patient support cushion 7 may be freely swung in and out of the recess without interfering with the border that defines the recess. That is, the edges of the patient support cushion 7 can't be configured to become blocked by the border of the recess or the patient support cushion 7 won't be able to swing between the swung in and swung out positions.

Preferably, the upper surface of the patient support cushion 7 moves in a plane that either is in common with an upper cushioned surface of the table or is parallel to the upper cushioned surface of the table. If the latter, the upper support cushion 7 may be slightly lower than that of the upper support cushion for the table.

Figure 3:
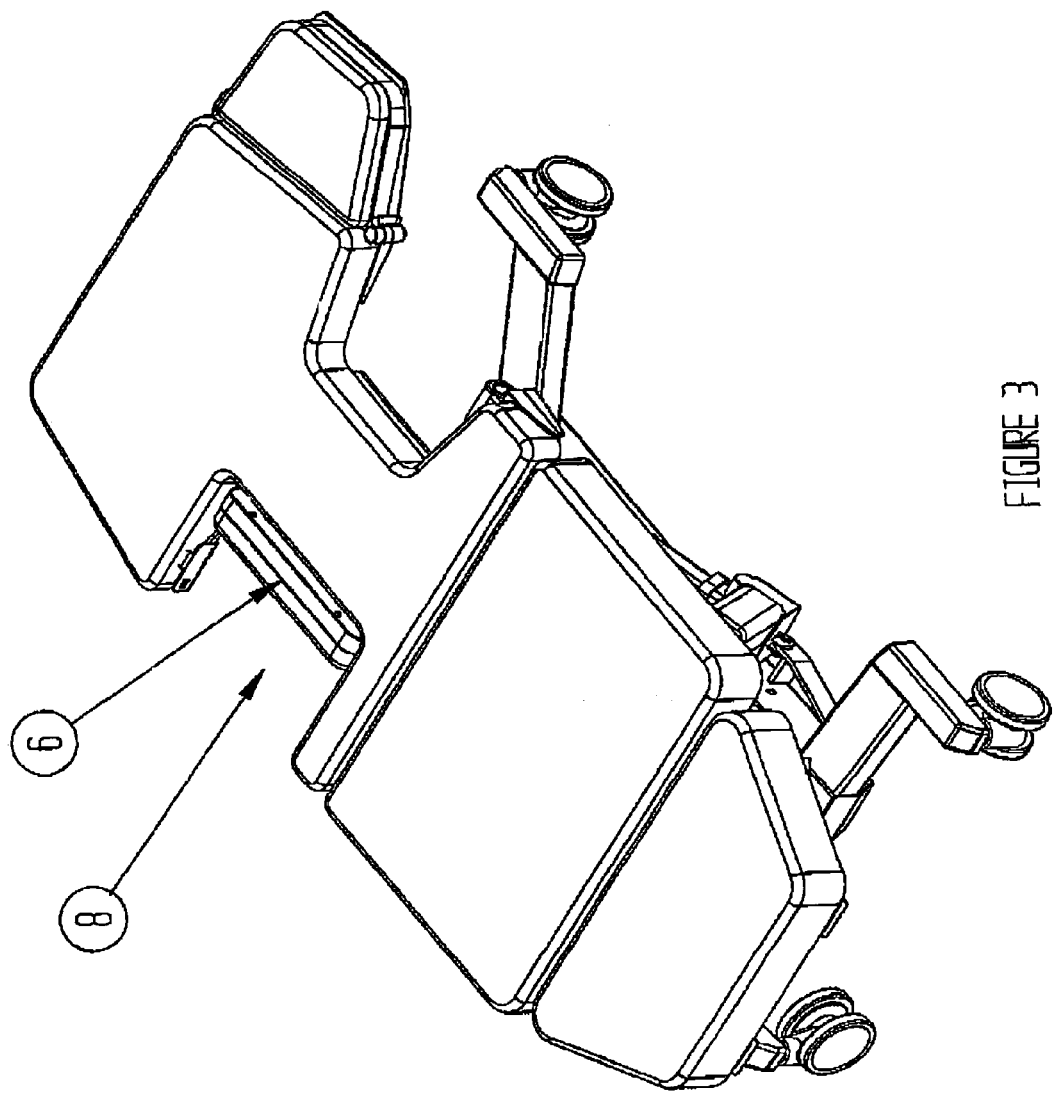

FIG. 3 shows the access cushion 6 rotated down into a dropped down orientation instead of rotated up. This creates the same opening 8 for the sonographer. Whether the access cushion 6 is down or up, the access cushion 6 is moved from the generally horizontal position to the generally vertical position. That is, the general vertical position is constituted, therefore, by the access cushion 6 reaching an upright orientation (rotated up) and by reaching a hanging down orientation (rotated down).

FIG. 4 shows how the patient support cushion 7 can be totally removed from the table if desired to create the same opening 9. The hinge pin 10 may simply slide out of the hinge knuckle 12 by lifting up on the patient support base 11.

Figure 5:
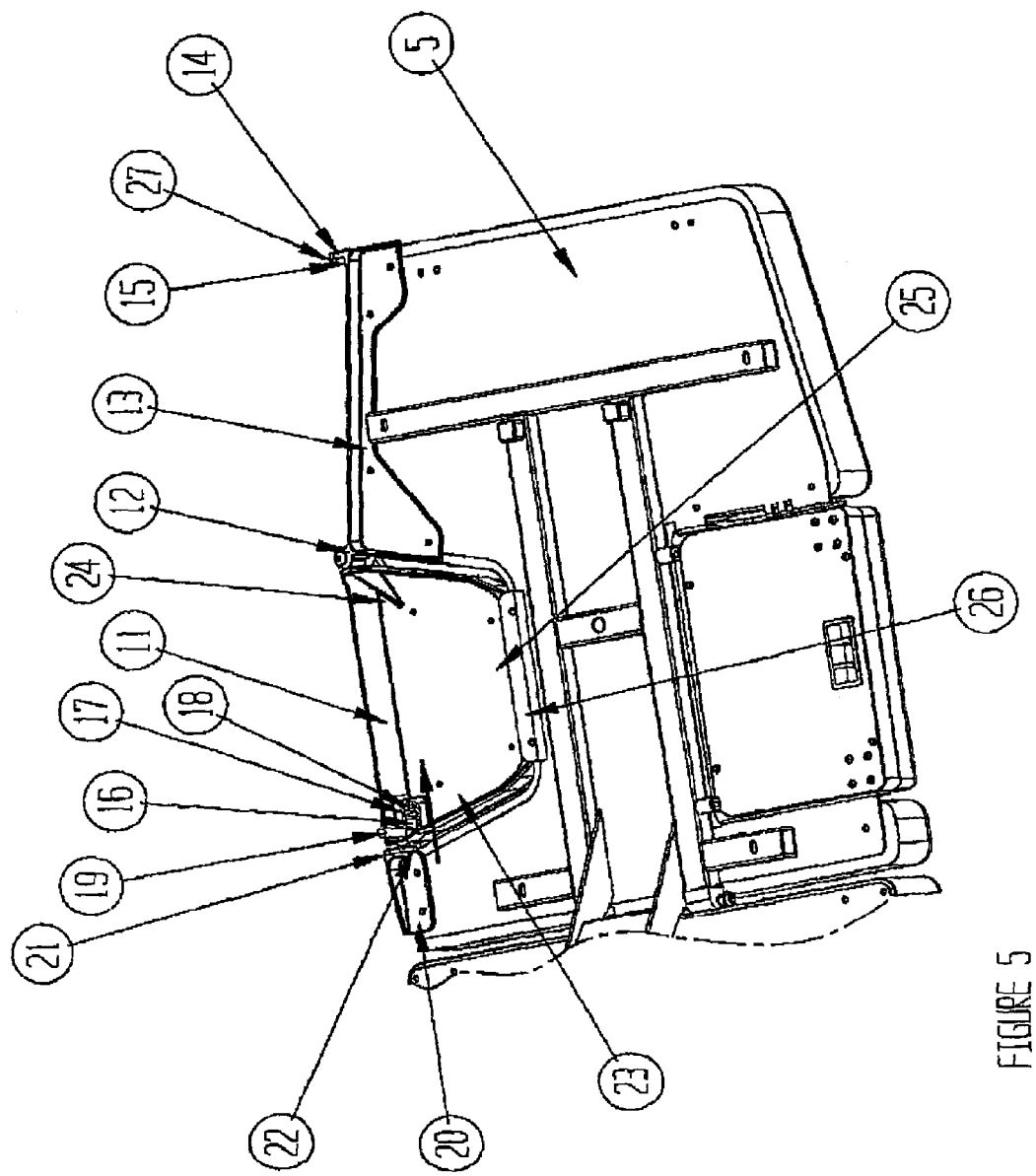
FIG. 5 is a partial isometric view of the table from below showing parts in detail of the swing out cushion for patient support.
Figure 6:
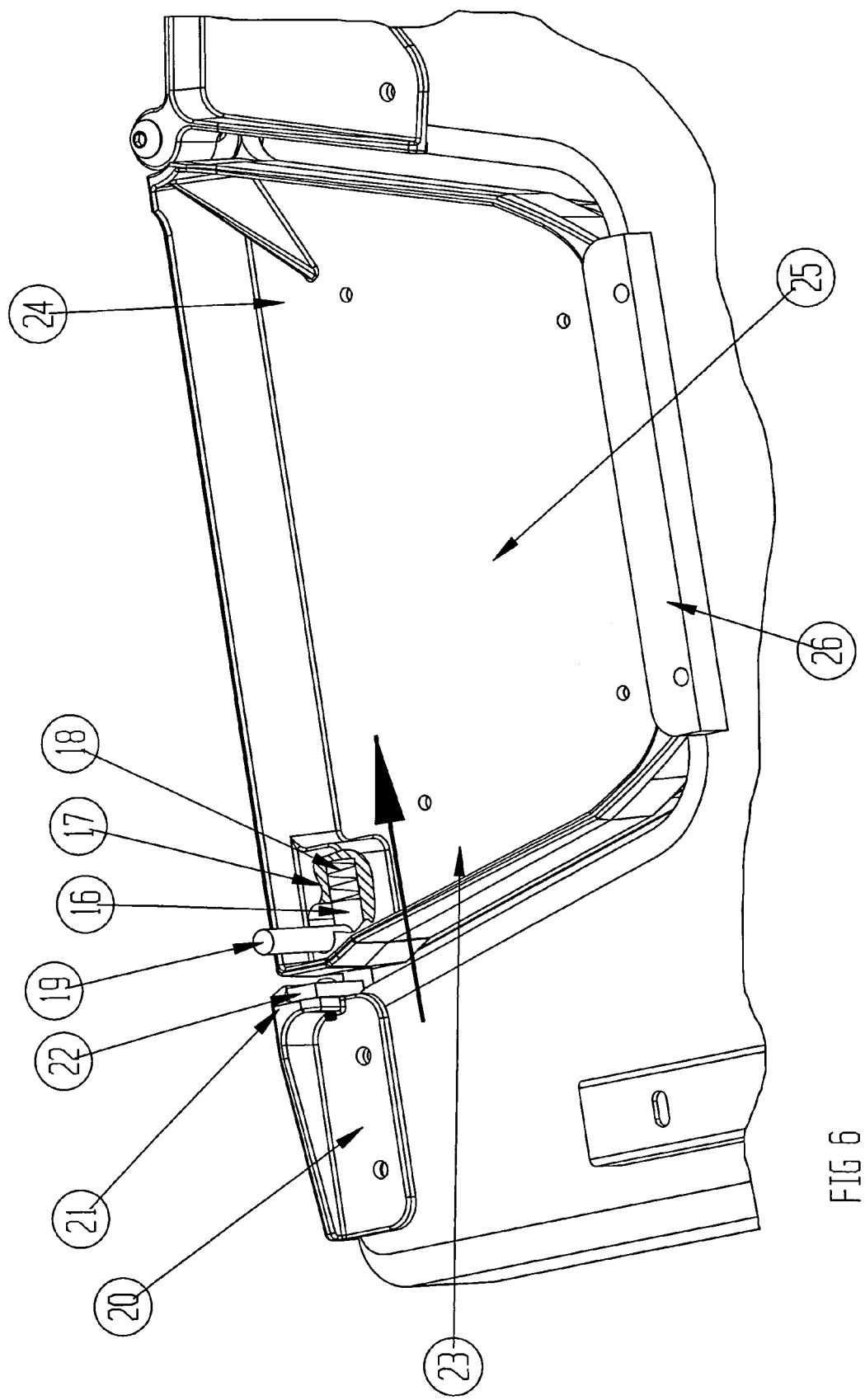
FIG. 6 is an enlargement of a portion of FIG. 5.

Referring to FIGS. 5, 6 and 1, looking at the underside of the fowler back assembly 5, the hinge knuckle 12 is an integral part of the hinge casting 13 which in turn is mechanically fastened to the fowler back assembly 5. At the head end of the hinge casting 13 is a catch 14 with an adjustable support block 15. FIG. 5 has a view of bottom of the patient support base 11 showing a pin 16 guided by a housing 17. A compression spring 18 applies force to the pin 16. Attached to the pin 16 is a pin handle 19. Also attached to the fowler back assembly is a catch casting 20 with an integral catch 21 and an adjustable support block 22.

In this position, the catch 21 holds the pin 16 in place and the support block 22 supports the pin such that the pin end 23 of the patient support cushion is held in and up when the patient's weight is applied. The hinge end 24 is likewise supported by the hinge knuckle 12. The inner edge 25 is supported by a lip 26 which is mechanically fastened to the fowler back assembly.

To swing the patient support cushion 7 out, the user pushes the pin handle 19 in the direction shown. This pulls the pin 16 out of the catch 21 so the cushion can be swung out. The pin handle 19, when so actuated, serves as a release to release the pin 16 from engagement with the catch 21. The patient support cushion 7 swings out until the pin 16 strikes the catch 14 on the head end. The tapered surface 27 on the catch forces the pin back into the housing 17 until the pin pops back out behind the catch lip. This holds it in place.

In this position, the pin rests on the support block 15 so the pin end is once again supported. In a similar fashion, the patient support cushion 7 can be released and swung back in. The pin 16 and the catch 21 are types of retainers that retain the patient support cushion 7 in the swung in and swung out positions by locking the patient support cushion 7 in a releasable manner in those positions. It should be understood that other kinds of conventional mechanical fasteners may serve as the retainers instead of using a pin and catch. Indeed, the retainers may be configurations of portions of either or both of the patient support cushion 7 and the table arranged to enable them to engage each other upon the patient support cushion 7 reaching the swung in position and upon the patient support cushion 7 reaching the swung out position.

As described, a cushioned table is provided with two elongated, opposite sides each with a respective recess. The patient support cushion 7 is movable about a pivot (pin 10, hinge knuckle 12) between a swung in position within the patient support recess and a swung out position that is substantially clear of the patient support recess. The pivot may be located partially or fully outside the patient support recess. The patient support cushion 7 preferably has a periphery that complements a shape of a border of the patient support recess.

The access cushion 6 is movable between a generally horizontal position in the access recess and a generally vertical position that is substantially perpendicular to the generally horizontal position. The access cushion 6 may be hinged to allow it to swing to an upright position, to a hanging position, or both. A pin and catch arrangement may be provided to lock the access cushion 6 in the generally horizontal and generally vertical positions. However, no pin and catch arrangement is needed for the hanging position. Alternatively, the access cushion 6 need not be hinged, but rather provision can be made to enable it to slide out of the recess for removal and subsequent re-insertion.

When the access cushion 6 is in its horizontal position and the patient support cushion 7 is in its swung in position, a patient may lie upon either or possibly both simultaneously while lying on the cushioned table between the two recesses. When the access cushion 6 is in an upright orientation and the patient support cushion 7 is in the swung out position, the patient may simultaneously rest his/her side on the cushioned table between the recesses, rest his/her back against the access cushion 6 and rest his/her arm on the patient support cushion 7. When the access cushion 6 is in the hanging down orientation and the patient support cushion 7 is in the swung in position, the patient may rest his/her side between the two recesses while resting his/her arm on the patient support cushion 7. The sonographer has closer access to the patient from the access recess with the access cushion 6 in the hanging down orientation than in the upright orientation.

While the patient support cushion 7 is depicted having a generally trapezoidal shape in cross-section (with rounded corners), other configurations are suitable provided the recess is configured to complement such other configurations. For instance, the patient support cushion 7 may have instead a semi-circular shape in cross-section or have only one side sloped outwardly rather than two (the other side may be perpendicular to that of the bases of the trapezoidal shape). The associated recess would have a complementary shape to the periphery of the cushion.

If desired, the patient support cushion 7 has a configuration that widens outwardly and has a periphery at least a portion of which complements in shape at least a portion of a border that defines the patient support recess. The dimensions and configuration of the patient support cushion 7 and the border are such that they provide sufficient clearance for the swinging movement of the patient support cushion 7 about the pivot and allows the patient support cushion 7 to substantially fill the empty space otherwise defined by the recess. There may remain slight gaps between the periphery of the patient support cushion 7 and the border of the patient support recess when the patient support cushion 7 is within the recess.

While described as a patient support cushion 7, the cushioning is preferable but may be omitted. Likewise, while the table is preferably cushioned, the cushioning may be omitted. When in the swung in position and when in the swung out position, the patient support or patient support cushion 7 is supported at two spaced apart locations, namely, at the location of the pivot and at the location of the pin 16 when engaged, respectively, to the catch 21 in the swung in position or the catch 14 in the swung out position. In addition, the patient support or patient support cushion 7 is supported at a third spaced apart location, i.e., the lip 26 when in the swung in position.

The patient support or patient support cushion 7 is stably supported at these locations in a manner sufficient to carry the portion of the body weight of the patient resting upon it. In the swung in position, the patient support or patient support cushion 7, when supported by the three spaced apart locations, may stably support as much as three times the load that it can stably support when in the swung out position where it is supported by only two spaced apart locations. For example, the patient support or patient support cushion 7 may stably support as much as 600 pounds in the swung in position and as much as 200 pounds in the swung out position.

While the foregoing description and drawings represent the preferred embodiments of the present invention, it will be understood that various changes and modifications may be made without departing from the scope of the present invention.

What is claimed is:

1. An apparatus suited to support a patient, comprising a table with a recess, a patient support movable about a pivot between a swung in position within the recess and a swung out position clear of the recess, the patient support being supported by the pivot in both in the swung in position and in the swung out position, the patient support being further supported at a support location spaced from the pivot in the swung in position and being supported at a further location spaced from the pivot in the swung out position, the recess extending inwardly from one side of the table, the table having a further side from which extends inwardly a further recess; and an access cushion in the further recess and movable about a hinge from a generally horizontal position within the further recess to a generally vertical position that is substantially perpendicular to the generally horizontal position.

2. An apparatus of claim 1, further comprising a plurality of retainers arranged so that applicable ones engage each other at the support location as the patient support reaches the swung in position to retain the patient support accordingly and applicable ones engage each other at the further location as the patient support reaches the swung out position to retain the patient support accordingly.

3. An apparatus of claim 2, wherein the applicable ones of the plurality of retainers include a common one engaging at both the support location and the further location.

4. An apparatus of claim 2, wherein the retainers include locking elements that lock the patient support at the support location and at the further location and that unlock under manual force.

5. An apparatus of claim 4, wherein the locking elements include two carried by the table and one carried the patient support.

6. An apparatus of claim 4, wherein the looking elements include a pin and a catch that are configured to engage each other, the pin being spring biased.

7. An apparatus of claim 1, wherein the patient support has at least one side that slopes outwardly.

8. An apparatus of claim 1, wherein the patient support has two sides that diverge outwardly.

9. An apparatus of claim 1, wherein the patient support widens in an outward direction.

10. An apparatus of claim 1, wherein the table and the patient support are cushioned.

11. An apparatus of claim 1, wherein each of the recesses extend inwardly toward each other.

12. An apparatus of claim 1, wherein the recess and the patient support each have respective peripheries that complement each other in configuration.

13. An apparatus of claim 1, wherein the pivot is arranged at least partially out of the recess.

14. An apparatus as in claim 1, wherein the table has a lip arranged to further support the patient support in the swung in position, the lip being spaced from the support location and from the pivot.

15. An apparatus of claim 1, wherein the patient support is releasable from the pivot to enable removal of the patient support cushion from the pivot entirely.

16. An apparatus suited to support a patient, comprising a cushioned table with a recess, a cushioned patient support movable about a pivot between a swung in position within the recess and a swung out position clear of the recess, the cushioned patient support being supported by the pivot in both in the swung in position in a generally horizontal plane and in the swung out position, the cushioned patient support being further supported at a support location spaced from the pivot in the swung in position and being supported at a further location spaced from the pivot in the swung out position, the cushioned table and the cushioned patient support having locking elements that engage to lock the cushioned patient cushion in the swung in position and to provide support at the support location and that engage to lock the cushioned patient cushion in the swung out position and to provide support at the further location.

17. An apparatus as in claim 16, wherein the table has a lip arranged to further support the cushioned patient support in the swung in position, the lip being spaced from the support location and from the pivot.

* * * * *